(12) United States Patent
Neuvonen et al.

(10) Patent No.: US 11,951,324 B2
(45) Date of Patent: Apr. 9, 2024

(54) METHOD AND SYSTEM FOR COMBINING ANATOMICAL CONNECTIVITY PATTERNS AND NAVIGATED BRAIN STIMULATION

(71) Applicant: Nexstim Oyj, Helsinki (FI)

(72) Inventors: Tuomas Neuvonen, Espoo (FI); Henri Hannula, Helsinki (FI)

(73) Assignee: Nexstim Oyj, Helsinki (FI)

( * ) Notice: Subject to any disclaimer, the term of this patent is extended or adjusted under 35 U.S.C. 154(b) by 0 days.

(21) Appl. No.: 17/331,669

(22) Filed: May 27, 2021

(65) Prior Publication Data

US 2021/0283412 A1    Sep. 16, 2021

Related U.S. Application Data

(63) Continuation of application No. 15/611,869, filed on Jun. 2, 2017, which is a continuation of application
(Continued)

(51) Int. Cl.
*A61B 34/20* (2016.01)
*A61B 5/00* (2006.01)
(Continued)

(52) U.S. Cl.
CPC ............ *A61N 2/006* (2013.01); *A61B 5/0042* (2013.01); *A61B 5/055* (2013.01); *A61B 5/4064* (2013.01);
(Continued)

(58) Field of Classification Search
None
See application file for complete search history.

(56) References Cited

U.S. PATENT DOCUMENTS

| 6,849,040 B2 | 2/2005 | Ruohonen et al. |
| 7,440,789 B2 | 10/2008 | Hannula et al. |

(Continued)

FOREIGN PATENT DOCUMENTS

| CN | 10149672 A | 8/2009 |
| CN | 101516444 A | 8/2009 |

(Continued)

OTHER PUBLICATIONS

Kosaka et al: Augmented Reality System for Surgical Navigation Using Robust Target Vision. Advanced Technology Research Center Olympus Optical Co., Ltd., 2000, IEEE, pp. 1-8.
(Continued)

*Primary Examiner* — Patricia J Park
(74) *Attorney, Agent, or Firm* — Laine IP Oy; Mark W. Scott (57) ABSTRACT

When operating a brain stimulation device, it is critical to understand and control the network effects associated with the area being targeted for stimulation. The combined system and methods provided herein provides the operator with a real-time view of the brain network potentially affected by the stimulation. The system and method are capable of increasing the accuracy of diagnostic information. Additionally, disclosed herein are a system and method for combining navigated brain stimulation data and anatomical data with brain connectivity data for an individual.

19 Claims, 6 Drawing Sheets

Related U.S. Application Data

No. 13/824,416, filed as application No. PCT/FI2012/050550 on Jun. 4, 2012, now abandoned.

(60) Provisional application No. 61/492,821, filed on Jun. 3, 2011.

(51) Int. Cl.
    A61B 5/055        (2006.01)
    A61B 6/03         (2006.01)
    A61B 6/50         (2024.01)
    A61N 2/00         (2006.01)
    A61N 2/02         (2006.01)
    A61B 5/06         (2006.01)
    A61B 5/389        (2021.01)

(52) U.S. Cl.
    CPC ............ *A61B 5/7425* (2013.01); *A61B 6/037* (2013.01); *A61B 6/501* (2013.01); *A61B 34/20* (2016.02); *A61N 2/02* (2013.01); *A61B 5/061* (2013.01); *A61B 5/389* (2021.01); *A61B 2576/026* (2013.01)

(56) References Cited

U.S. PATENT DOCUMENTS

| | | | |
|---|---|---|---|
| 7,720,519 | B2 | 5/2010 | Ruohonen |
| 7,925,066 | B2 | 4/2011 | Ruohonen et al. |
| 2003/0050527 | A1* | 3/2003 | Fox ................. A61N 2/006 600/13 |
| 2004/0122706 | A1 | 6/2004 | Walker et al. |
| 2004/0138550 | A1 | 7/2004 | Hartlep et al. |
| 2005/0075560 | A1 | 4/2005 | Hannula et al. |
| 2006/0017749 | A1 | 1/2006 | McIntyre et al. |
| 2008/0031847 | A1 | 2/2008 | Cohn et al. |
| 2008/0058581 | A1 | 3/2008 | Aho |
| 2008/0058582 | A1 | 3/2008 | Aho et al. |
| 2008/0064950 | A1 | 3/2008 | Ruohonen et al. |
| 2008/0262338 | A1* | 10/2008 | Paitel ................. A61B 5/743 600/409 |
| 2009/0005678 | A1 | 1/2009 | Schmiedehausen et al. |
| 2010/0036453 | A1* | 2/2010 | Hulvershorn ........ A61B 5/4064 607/45 |
| 2010/0113959 | A1* | 5/2010 | Pascual-Leone ...... A61N 2/008 600/13 |
| 2010/0185042 | A1 | 7/2010 | Schneider et al. |
| 2010/0185256 | A1* | 7/2010 | Hulvershorn ......... A61N 1/361 607/45 |
| 2010/0324440 | A1* | 12/2010 | Moore .................. A61B 5/377 600/544 |
| 2011/0270345 | A1 | 11/2011 | Johnston et al. |
| 2012/0083647 | A1* | 4/2012 | Scheinin ............. A61N 5/0622 607/101 |
| 2012/0087559 | A1* | 4/2012 | Hellier .................... A61B 5/05 382/128 |

FOREIGN PATENT DOCUMENTS

| | | |
|---|---|---|
| CN | 101535828 A | 9/2009 |
| JP | 2003126056 A | 5/2003 |
| JP | 2004000636 A | 1/2004 |
| JP | 2006340774 A | 12/2006 |
| JP | 2009006145 A | 1/2009 |
| JP | 2010503439 A | 2/2010 |
| WO | WO2008031847 A1 | 3/2008 |
| WO | WO2007123147 A1 | 9/2009 |
| WO | WO2012117166 A1 | 9/2012 |

OTHER PUBLICATIONS

Lazar et al: Investigation of Anatomical and Effective Connectivity using White Matter Tractography and Transcranial Magnetic Stimulation. Proc. Intl. Soc. Mag. Reson. Med., 2005, vol. 13.

* cited by examiner

METHOD AND SYSTEM FOR COMBINING ANATOMICAL CONNECTIVITY PATTERNS AND NAVIGATED BRAIN STIMULATION

FIELD OF INVENTION

The present invention relates to the mapping of brain functions and treating disorders using a brain stimulation system and in particular the determination of anatomical and functional relationships in the brain.

BACKGROUND OF THE INVENTION

The aim of operating a brain stimulation device on a patient's brain may be to either cause an evoked response for diagnostic purposes, or to cause a transient or permanent change in the brain function for therapeutic purposes. The effectiveness of a brain stimulation method depends on how well the stimulating device and the stimulating energy reach the intended anatomical region being targeted.

One solution is to use a stereotactic arrangement to accomplish a positioning of stimulation equipment in relation to the targeted anatomical portions of the body. Typically stereotactic navigation devices use anatomical images (structural images from MRI or CT) to correlate stereotactic instruments to individual anatomy. However, many times the brain anatomy of a subject undergoing stimulation has been altered or damaged by trauma or tumor. As such, an anatomical image of the subject's brain may not be sufficient to determine the functionality of certain portions of the brain.

Diagnostic or therapeutic stimulation may have local or long-range effects, depending on the anatomical and functional relationship of the targeted area. As such, there exists a need for a method and system for providing the operator of a stimulation device with an accurate view of the underlying anatomy, connections and functions specific to an individual's brain.

SUMMARY OF THE INVENTION

It is an aspect of certain embodiments of the present invention to provide an operator of a navigated brain stimulation system with a more complete and realistic view of the potentially affected brain network by the stimulation.

It is a further aspect of certain embodiments to provide a system and method capable of increasing the accuracy of diagnostic information.

Still yet, it is an aspect of certain embodiments to combine navigated brain stimulation with brain connectivity data from an individual.

According to certain embodiments of the present invention there are described herein methods for combining stimulation navigation with functional data. These methods are capable of being implemented with invasive brain stimulation or, preferably, with non-invasive transcranial stimulation. Such methods comprise some or all of the following steps: acquiring one or more anatomical image of a brain, acquiring functional data of the brain and combining the anatomical image with the functional data. Examples of anatomical images are MRI images and CT images. Examples of functional data are positron emission tomography (PET) data, functional magnetic resonance imaging (fMRI) data, and diffusion tensor imaging (DTI) data.

Furthermore, a system according to certain embodiments of the present invention comprises a stereotactic device that can be used to guide a stimulating device with respect to the brain anatomy. A navigation device can be used to guide the stimulating device to an appropriate anatomical location where the stimulating device is activated and induces an E-Field on or in a portion of the brain.

In accordance with certain embodiments, it is possible to reduce the uncertainty associated with existing brain mapping methods, in particular that of image-guided (navigated) transcranial magnetic stimulation and white matter fiber tracking provided by appropriate techniques. Additionally, it is possible to aid in the planning of therapeutic intervention e.g. surgery, placement of a cortical or deep brain stimulator device. Still yet, embodiments of the present invention make resections safer by integrating information from different imaging modalities currently in use. Furthermore, embodiments of the present invention help render surgical decision making objective by offering quantitative information from different diagnostic modalities.

Embodiments of the present invention describe a stimulating device connected to a navigation system comprising a real-time physics-modeling system and a connectivity tracking system. The combined system provides the operator with a real-time view on the brain network potentially affected by the stimulation. Additionally, not only can the stimulating device be modeled, but also the predicted effect of the stimulating device can be modeled and displayed.

According to an aspect of certain embodiments, it is advantageous to supply a stereotactic positioning system with display of functional data, such as positron emission tomography (PET) or functional magnetic resonance imaging (fMRI), to highlight functionally active areas relevant to the procedure. Further, advances in the MRI technique called diffusion tensor imaging (DTI) has made it possible to map local and remote anatomical connections formed by cerebral white matter. Adding anatomical connectivity information to a positioning part of a brain stimulation device to enrich the information available to the operator leads to better understanding of diagnostic information and more informed targeting of, for example therapeutic stimulation.

When operating a brain stimulation device, it is critical to understand and control the network effects associated with the area being targeted for stimulation. The combined system provides the operator with a real-time view on the brain network potentially affected by the stimulation.

DETAILED DESCRIPTION OF EXEMPLARY EMBODIMENTS

A computer assisted stereotactic positioning system associated with a stimulating device can be used to determine portions of the central nervous system targeted by the stimulation either to guide the placement of a stimulation probe or to explain the diagnostic information or effects caused by the stimulating device.

Different technical restrictions apply to invasive and noninvasive stimulation devices. Invasive stimulation devices can be placed in direct contact with the tissue being stimulated. Invasive devices are assumed to directly activate the tissue being in direct contact with the stimulating probe.

Non-invasive stimulation devices must typically rely on crude approximations of stimulation effects or rely on real-time or offline modeling of stimulation effects. Invasive techniques may use real-time or offline modeling and approximations of stimulation effects in particular for planning of installation of implantable devices and adjustments to stimulation parameters after installation and/or a trial period.

The following are several non-limiting examples of real-time and/or offline modeling. For example, an activating function (AF) can be determined to approximate the volume of activation around a deep brain stimulation (DBS) probe. An activation function describes the electric field induced by the stimulation probe, wherein the volume and shape of the electric field leading to activation depends on many device parameters. Depending on the observed or predicted effects caused by the activation of the stimulation device, the operator may wish to change stimulation parameters to match a desired stimulating field pattern which better matches the underlying anatomical structures.

Another example is given from the field of transcranial magnetic stimulation (TMS). A computer aided stereotactic system can be used in positioning a coil above an appropriate anatomical area. A physics modeling system or program can then be used to model the effects of a TMS coil, displaying the coil activation pattern on the brain surface or at one or more depths within the brain. Typically, a TMS coil activation pattern has a stimulation focus, i.e. an area that has a higher concentration of electric field than the surrounding areas. The size of the area experiencing supra-threshold stimulation varies according to the stimulator output. This region is the activation area (AA) or activation volume (AV).

An example of a connectivity tracking system is given. Anatomical connections between brain areas can be studied using a technique called diffusion tensor imaging (DTI). DTI is based on the imaging of water diffusion using magnetic resonance imaging. Using several images sensitive to water diffusion and mathematical post-processing of the images, it is possible to display preferred direction of water diffusion in one or more image volume element(s) (e.g. voxel(s)).

It has been shown that cerebral white matter axons passing through a voxel are aligned with a preferred direction of diffusion. Further, it is possible to construct visualizations of virtual axons bundles or fibers using one or more mathematical means. This technique is referred as (white matter) fiber-tracking in the literature.

A typical fiber tracking algorithm, e.g. tractography algorithm, utilizes firstly diffusion sensitive MR data and some parameters defining the boundary conditions for the algorithm, e.g. starting and stopping criteria, step length, upper limit to fiber length, possible fiber curvature limits etc. The aim is to help the algorithm to find physiologically meaningful fibers. The list of possible parameters and their values is known to those skilled in art.

A fiber-tracking algorithm can generate any number of fibers from a given data, but often only the visualization of anatomically relevant fiber bundles is desired. Typically the operator sets a starting point (A) and a stopping point (B) for the tracking or visualization system. As a result, only those fibers connecting A to B (or vice versa) and satisfying boundary conditions are visualized. Setting a target region can be simple or tedious. Based on the known subcortical anatomy, it is possible to identify some major structures, such posterior limb of internal capsule (PLIC) or pons, through which fibers from motor cortex are descending. However, setting cortical target regions is far more difficult and less obvious. Further in the presence of cortical or subcortical lesions, setting of meaningful target regions (A or B) may be difficult.

Embodiments of the present invention describe a stimulating device connected to a navigation system comprising a physics-modeling system (real-time or offline) and a connectivity tracking system. The effect of certain embodiments is that the volume of the activating function (AF) as described in the literature for DBS can be used as defining the target region (A or B). Similarly, for TMS or other non-invasive stimulation methods, the activation volume or activation area can be used for defining the target region (A or B). Examples and embodiments are described in more detail below.

An example of the present invention relating to white matter tractography based on navigated brain stimulation results is provided herein.

The integration of anatomical and functional studies allows, for example, for safer resection of brain tumors located in close proximity to eloquent areas. A multimodal software solution, e.g. iPlan Cranial software, Brainlab AG, Feldkirchen, Germany, allows integration and correlation among preoperative and intraoperative anatomical and functional data for comprehensive planning of neurosurgical procedures. The clinical value of the planning software is dependent on the accuracy and reliability of the patient data entered.

Diffusion tensor imaging (DTI) and white matter fiber tractography are accepted MR-imaging techniques utilizing the concept of anisotropic water diffusion in myelinated fibers. Tractography enables 3D reconstruction and visualization of white matter tracts and provides information about the relationship of these tracts to, for example, the eloquent areas and any lesion.

An important challenge for reconstructing white matter fibers is the definition of a functionally meaningful seed area for starting the tracking process. In patients with brain tumors, the functional neuroanatomy of the patient may be significantly affected by the lesion which makes it difficult to define seed areas based solely on anatomical landmarks.

Navigated Brain Stimulation (NBS), also known as navigated Transcranial Magnetic Stimulation (TMS), can be used for accurate, noninvasive mapping of portions of the brain, such as the motor cortex. NBS functional mapping data can be directly input into surgical or treatment planning software, such as the iPlan software solution. Additionally, the NBS data can be used as an aid in selecting originating seed areas for white matter tractography.

NBS is a noninvasive technique for electrocortical stimulation. Instead of generating an electric field from electrodes placed on the exposed cortex, as in intraoperative direct electrocortical stimulation (DCS), with NBS the electric field (E-field) is induced intracranially by triggering a transcranial magnetic stimulation (TMS) coil placed externally to the head.

When determining motor functions, the simultaneous measurement of motor evoked potentials (MEP) by electromyography (EMG) can be used to identify and verify the motor representation areas in the cortex, in the same manner as with DCS. Excellent resolution of the motor representation areas can be achieved by using a purpose-built figure eight coil and adjusting the field strength to the individual patient's motor threshold.

Similarly, other functions can be determined and mapped via appropriate methods. For example, when determining speech and/or cognitive functions a task can be presented to the subject and the subject's response to the task can be measured/determined before, during and/or after navigated TMS stimulation. Examples of cognitive mapping via NBS can be found in PCT/FI2012/050218 filed Mar. 5, 2012 and U.S. Provisional application 61/448,676 filed Mar. 3, 2011, both of which are herein incorporated by reference in their entirety.

Compared to DCS, NBS mapping has the advantage that it is noninvasive and can therefore be used preoperatively as an aid in surgical planning and reviewing patient selection for surgery or other therapeutic options.

Mapping with NBS is fully compatible with the surgical navigation paradigm since the same MRI dataset can be used as an anatomical image as the basis of both presurgical planning and intraoperative guidance. In NBS mapping the MRI dataset can be used to link the location of the TMS-generated E-field to the individual patient's cortical anatomy. Using familiar stereotactic navigation techniques, moving the TMS coil guides the E-field location through the intracranial structures. The MRI dataset can be rendered three dimensionally by the NBS System which can be a helpful feature for orientation and location of the cortical somatotopy with respect to the intracranial anatomical structures.

DICOM-export of motor response maps can be exported from the NBS System which permits integration of NBS mapping data with other modalities within, for example, the iPlan software.

Functional mapping of the motor cortex was performed with the NBS System. The data file of the mapping session was retrieved from the NBS System via an NBS planning station for post-processing. The maximum E-field locations were selected and verified before the motor mapping image—generated from the corresponding MEP responses—was exported in DICOM format to a portable memory device.

Figure 1:
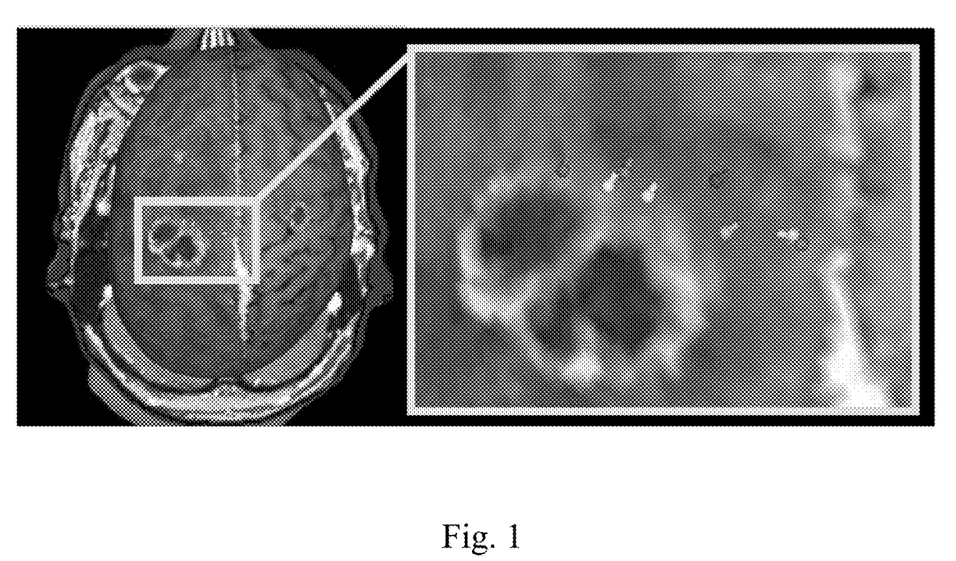
FIG. 1 shows stimulated E-field locations recorded in a mapping session as displayed on an NBS System (left). NBS software calculates the maximum E-field locations within the cortex and color-codes them according to their corresponding peak-to-peak MEP amplitudes, making a heat map. Locations eliciting the largest MEPs are color-coded white in the heat map (enlarged image, right).

FIG. 1 shows an example of Stimulated E-field locations recorded in a mapping session as displayed on NBS System. The NBS software calculates the maximum E-field locations within the cortex and color-codes them according to their corresponding peak-to-peak MEP amplitudes, making a heat map. Locations eliciting the largest MEPs are color-coded white in the heat map. An expanded view of the area surrounding a tumor, including the color-coded maximum E-field locations is shown on the right of the figure.

Figure 2:
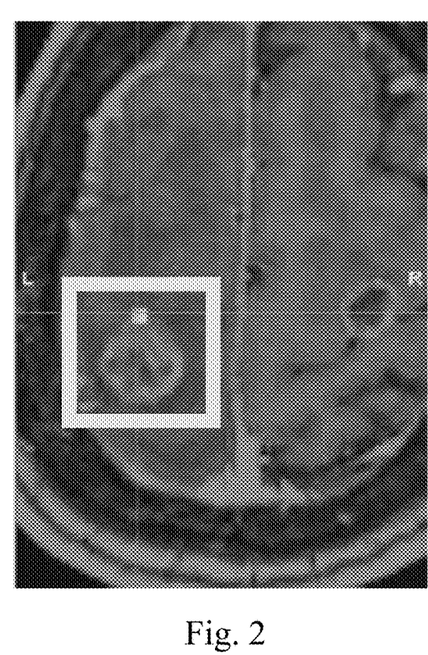
FIG. 2 shows a DICOM-export of a hot spot stimulation location visualized on an NBS screen. The MEP maximum response for the largest hand muscle, abductor pollicis brevis (APB), is defined as the "hot spot" to be used as a seed region for tractography of the pyramidal tract. The APB hotspot is in the immediate vicinity of the tumor.

From the mapping session a DICOM-export of stimulation locations visualized on the NBS screen can be generated. In the present example, the MEP maximum response for the largest hand muscle, abductor pollicis brevis (APB), is defined as the "hot spot" to be used in planning software as the seed region for tractography of the pyramidal tract. The APB hotspot in the present example is in the immediate vicinity of the tumor, shown and highlighted in FIG. 2.

Figure 3:
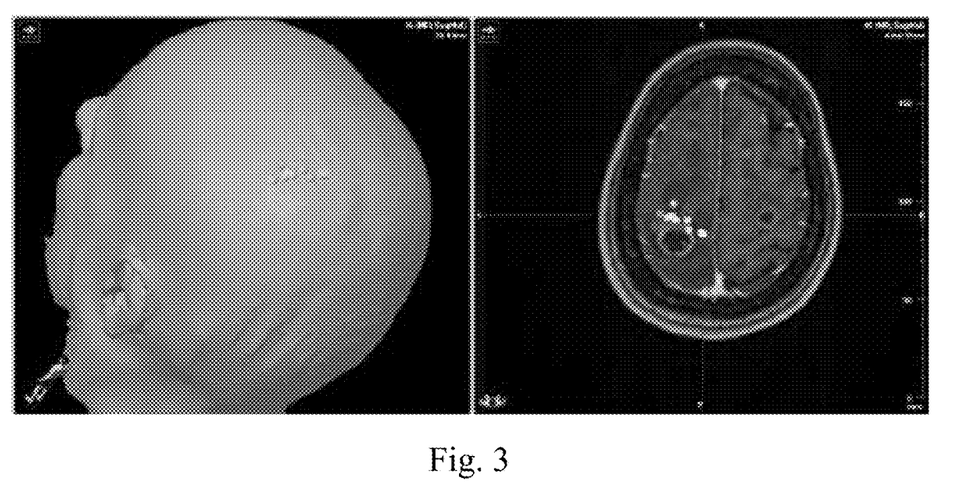
FIG. 3 shows a patient's MRI dataset, NBS mapping image and DT-imaging data combined. Following image fusion, MEP maps from the NBS motor mapping session are displayed in the 3D navigational image and can be used as seed regions for applying the tractography algorithms to visualize the white matter tracts from the primary motor cortex. The location of the largest MEP response for the APB muscle used for the seed regions is color-coded green.

The patient's MRI dataset, NBS mapping image and DT-imaging data were then uploaded to iPlan planning software. Following image fusion, MEP maps from the NBS motor mapping session are displayed in the 3D navigational image, as shown in FIG. 3. The indicated locations of motor activity can be used as seed regions for applying tractography algorithms to visualize the white matter tracts from the primary motor cortex. The location of the largest MEP response for the APB muscle used for the seed regions is color-coded green in the figures.

Figure 4:
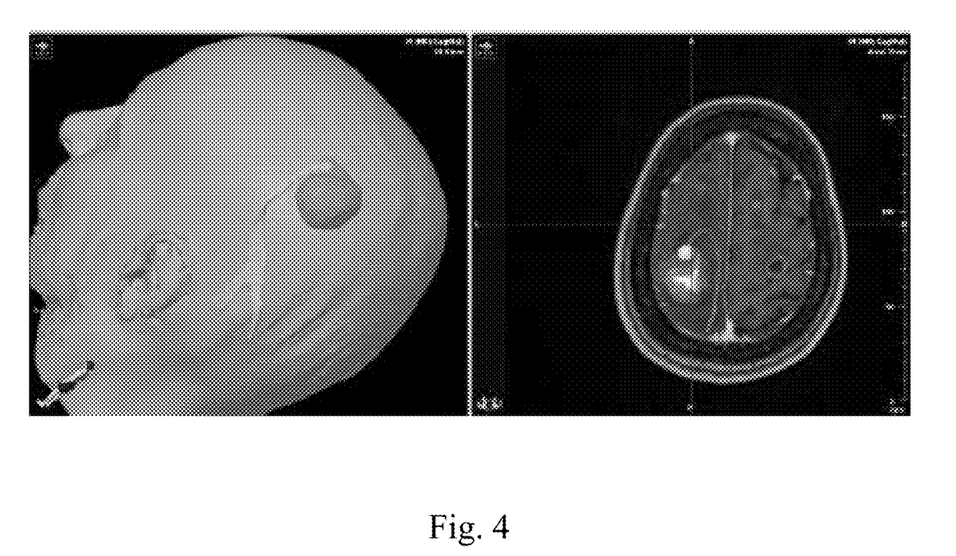
FIG. 4 shows a visualization of fibers originating from the APB hot spot of FIG. 2 after converting the tractography results, without any postprocessing, into a 3D object for export to a navigation system. The tumor is marked in red and the APB hotspot is visualized as yellow sphere.

FIG. 4 shows the visualization of fibers originating from the APB hot spot after converting tractography results—without any postprocessing—into a 3D object. The 3D object may then be export to, for example, a Brainlab navigation system. Additionally, the planning may take place in real time within an NBS system. In the figure, the tumor is marked in red and the APB hotspot is visualized as yellow sphere.

Functionally meaningful seed areas are reliably determined from the non-invasive NBS motor mapping data and permitted a more specific white matter fiber construction process.

The study illustrated that accurate and reliable noninvasive motor mapping data can greatly facilitate tractography. DICOM export of NBS motor mapping data can be sent to a planning system to select seed areas. Additionally, planning software can be integral within the NBS system in order to produce real-time visualization of white matter fiber's to the operator based on selected seeds. These methods can remove a key obstacle to the wider clinical application of DT-imaging and tractography by allowing, for example, quick, accurate, meaningful and reliable seed selection.

NBS-guided fiber tractography can be realized as a multimodal technique for preoperatively generating functionally-relevant white matter networks and validating the reconstructed fibers, as described in the example above. Additionally, NBS can add functionality to existing and novel planning systems for planning surgical trajectories that can help preserve critical subcortical motor pathways, as well as cortical motor areas, for example during tumor resection.

According to certain embodiments of the present invention it is desirable to associate activating function(s), activating volume(s) and/or activating area(s) with a fiber tracking algorithm.

A method according to such embodiments can comprise some or all of the following steps; initiating stereotactic tracking of one or more tools, preparing diffusion weighted MR data for fiber tracking, matching diffusion data to a stereotactic frame, identifying an activating function (AF), activation area (AA) or activating volume (AV) in the stereotactic space, using the AF, AA or AV for determining a target region (A or B), and display the resulting fibers.

Preparing diffusion weighted MR data for fiber tracking can include, for example, image matching, eddy current correction, diffusion tensor estimation or a combination thereof. For matching diffusion data to a stereotactic frame the system can us coregistration of an anatomical MRI and the diffusion MRI. Image matching and coregistration can be accomplished by identifying anatomical landmarks from multiple images and/or data sets and aligning similar/identical landmarks. Additionally, in order to identifying the AF, AA or AV in real time the system may include physics modeling of the stimulation device.

Methods are provided herein for combining stimulation navigation with functional data. These methods are capable of being implemented with invasive brain stimulation or, preferably, with non-invasive transcranial stimulation. Such methods comprise some or all of the following steps: acquiring one or more anatomical image of a brain, acquiring functional data of the brain and combining the anatomical image with the functional data. Examples of anatomical images are MRI images and CT images. Examples of functional data are positron emission tomography (PET) data, functional magnetic resonance imaging (fMRI) data, and diffusion tensor imaging (DTI) data.

In order to combine the functional data of the brain and the anatomical image it may be desirable to identify common landmarks between the anatomical image and the functional data. The anatomical image and functional data may be combined by coregistering at least a portion of the functional data, said portion being associated with a portion of interest of the brain, with the corresponding location from the anatomical image with the aid of the common landmarks. Furthermore, the combined view of the brain can be stereotactically aligned with transcranial magnetic stimulation (TMS) navigation software.

The order in which the anatomical image, functional data and TMS data are combined and/or coregistered can vary. Additionally, it may be desirable for all of the data to be combined with each other or it may be sufficient for some data to be only combiner or coregistered with one other type of data. For example, the anatomical image, functional data and TMS data may be coregistered only with a stereotactic frame utilized by TMS navigation software. Therefore, individually the functional data is not directly combined with the anatomical image, but the data is indirectly combined via the stereotactic frame.

Additionally, it is desirable to display a combined view of the brain having functional data for at least a portion of interest of the brain associated with the corresponding location on the anatomical image and TMS data. The anatomical image of the brain can also be stereotactically aligned with a subject's head using TMS navigation software.

When operating a brain stimulation device, it is critical to understand and control the network effects associated with the area being targeted for stimulation. The combined information can provide the operator with a real-time view on the brain network potentially affected by the stimulation. Therefore, with a more complete and realistic view of the potentially affected brain network by the stimulation, it is possible for the operator to better select a location of the brain to target with a TMS pulse based on the combined view.

As discussed above, the location on, or within, the combined view can be tagged with a brain function determined from navigated TMS. The location may be a point or area on a surface of the brain or it may be a three-dimensional volume on or within the brain. By stimulating a plurality of particular points within an area of interest, for example by a grid or other arrangement, and tagging those areas with a desired response or function it is possible to map a portion of the brain using navigated TMS based on the combined view. Additionally, at least some of the mapping for a particular region may be done on a regular view, e.g. anatomical image, standard head model, etc. and the data can be added or incorporated with the anatomical image when creating the combined view. The area to be mapped may be determined based on the function data.

The incorporation of the functional data with the anatomical image allows for superior seed selection, as discussed above. Therefore, it can be desirable to select a seed region, within a navigated TMS mapped region, from the combined view for applying a tractography algorithm. The tractography algorithm can then be used to determine white matter tracts. The white matter tracts can then be added to the combined view, as is shown by FIG. 4.

An advantage to certain embodiments of the present invention is to provide the tractography algorithm calculation in real-time and to display the results to a navigated TMS operator during stimulation. However, the present methods can also be used to apply the tractography algorithm in an off-line mode. Such embodiments can be used for surgical or treatment planning, for example.

As discussed above, by using a seed location and a tractography algorithm it is possible to determine white matter tracts extending from the seed location to a distal, terminal end or ends. The terminal ends can include a deep target and/or a distant target as shown in FIG. 7.

Figure 7:
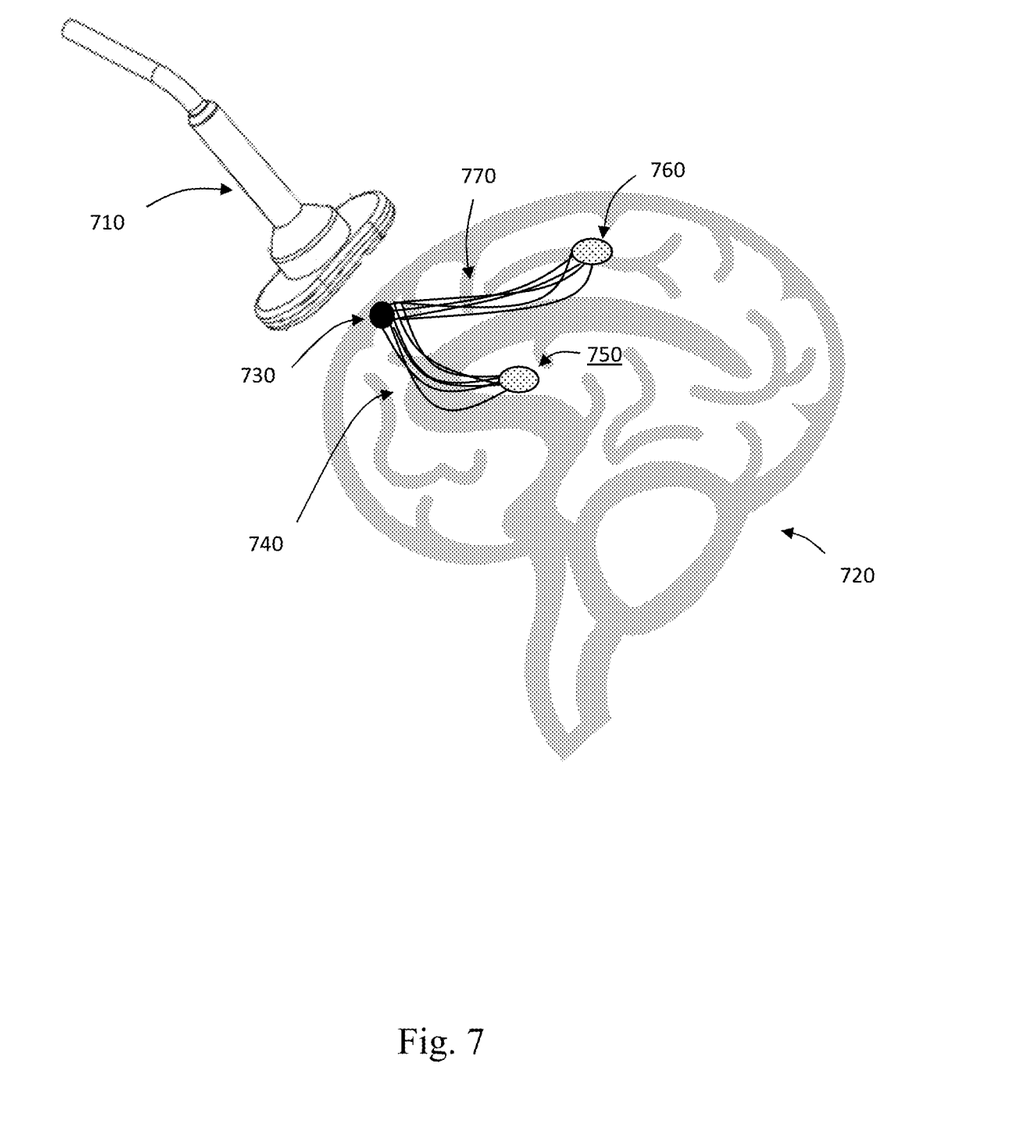
FIG. 7 shows an example of the concept of connections between a seed location and deep and distant targets within the brain.

FIG. 7 shows a representation of the present concept. A TMS coil 710 is used to produce an E-field hot spot 730 at an initial location on or within the patient's brain 720. The location of the E-field hot spot 730 can be rendered on a head model for an operator from physics modeling. The figure shows representatively how white matter fibers 740 link the location of the E-field hot spot, which is at or near the surface of the brain, to a deep target 750 within the brain. Similarly, white matter fibers 770 link the location of the E-field hot spot to a distant target at another location, often at or near the surface of the brain. DTI and fiber tracking modules are capable of generating renderings of the white matter connections and locations of the targets for displaying to the operator.

Figure 8:
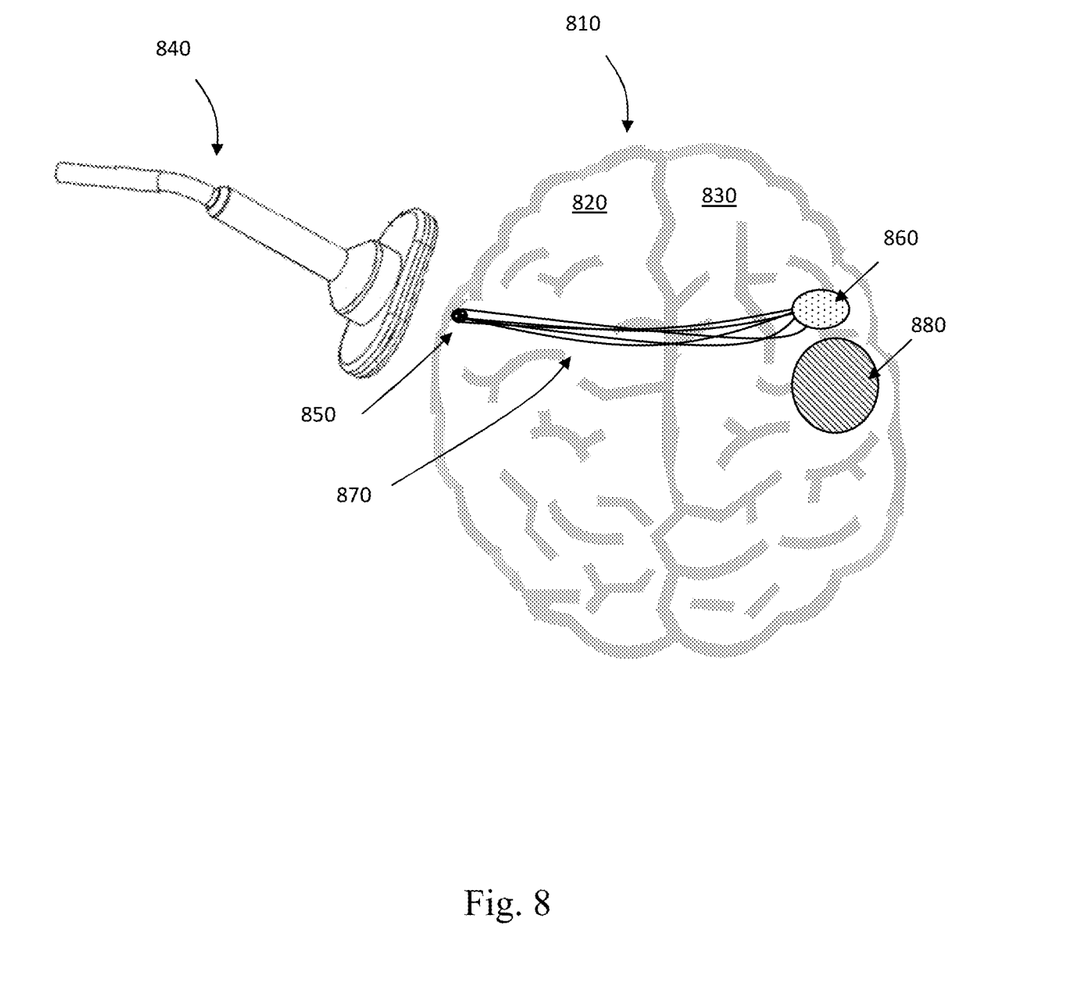
FIG. 8 shows an example of the concept of transcallosal white matter fibers linking the two hemispheres of the brain.

A distant target, as shown in FIG. 8, can even be in the opposite hemisphere from the seed. As representatively shown in the figure, a TMS coil 840 stimulates a location 850, for example, at or near the surface of the brain 810 on the left hemisphere 820. Physics modeling can render the location of the E-field hot spot 850. In the present example, the presence of a tumor or lesion 880 may make the stimulation of areas around the area difficult, unreliable or undesirable. Therefore, through DTI and fiber tracking it is possible to locate Transcallosal white matter fibers which link distant locations in one hemisphere, 820, to the opposite hemisphere, 830. As such, it is possible to indirectly stimulate a target area 860 in hemisphere 830 by directly stimulating the location 850, which is unobstructed, in hemisphere 820.

One method for verifying that a seed is a desired seed is to stimulate an area of the brain corresponding to a terminal end of white matter tracts determined by the tractography algorithm. If stimulation of the terminal end(s) produces a desired response then it is possible to verify the seed, distant/deep target and white matter tracts/fibers connecting the two. Similarly, if stimulation of the terminal end(s) does not produce the desired response then there is a chance that the seed, determined white matter tracts/fibers and/or targets are not proper. In such situations it may be desirable to stimulate the terminal end several times with varying stimulation parameters. Additionally or alternatively, some or all of the method steps for determining the terminal end can be repeated with a different seed and/or tractography algorithm/ tractography algorithm parameters, There is also presented herein a method for providing stimulation to a desired location in the brain of a subject indirectly by stimulating a different location intracranially connected to the first. Such methods may include some or all of the method steps listed above with regards to combining stimulation navigation with functional data. Additionally, such methods described above with regards to combining stimulation navigation with functional data may include some or all of the following steps. Such methods comprise the steps of; identifying a first region of interest of the brain, said first region typically being associated with a particular function, identifying a second region of interest of the brain intracranial connected to said first region, wherein identifying the second region of interest can be based at least on the combined view, navigated TMS mapping data or portion of the methods described above, and indirectly stimulating the first region of interest of the brain by applying stimulation to the second region of interest of the brain. For the sake of the present methods, the first and second regions should be distant and connected via white matter tracts as described above.

According to such methods, the method may be for and/or include applying a direct and/or indirect stimulation. For example, the applied stimulation can be at least one TMS pulse, a plurality of TMS pulses from a TMS coil or a deep brain stimulation, for example a DBS probe.

In particular, for a method for use in surgical or treatment planning utilizing a DBS probe, the method may further comprise the step of determining an activating function which approximates the volume of activation around a terminal end of one or more white matter tracts. Based on this at least one deep brain stimulation probe stimulation parameter can be determined based on the activating function.

The methods described above can be for determining and displaying white matter tracts pre or post stimulation. For example, navigated TMS can be used to map a region of the brain to determine a particular location of the brain which elicits a desired or the greatest response to stimulation. Once the location which is to be used as a seed has been located through this mapping then the particular seed can be selected and used in the tractography algorithm. Such a method may intend to ensure that the seed used to determine the white matter tracts is actually responsible for a particular function. However, the present method can also be utilized to predict responses and white matter tracts in order to give the operator of a navigated brain stimulation system a better visual understanding of the underlying anatomy and functional relationships of the subject's brain.

As such, there are described herein methods for displaying predicted intracranial connections for navigated brain stimulation. Such methods may include some or all of the method steps listed above with regards to combining stimulation navigation with functional data and for providing stimulation to a desired location in the brain of a subject indirectly by stimulating a different location intracranially connected to the first. Additionally, such methods described above with regards to combining stimulation navigation with functional data and for providing stimulation to a desired location in the brain of a subject indirectly by stimulating a different location intracranially connected to the first may include some or all of the following steps. Such methods comprise the steps of; tracking a navigated TMS coil in relation to a subject's head, wherein the location and orientation of the subject's head is co-registered with at least a portion of the combined view, e.g. with the anatomical image or combined view as a whole, determining a predicted stimulation which would be applied to the subject by the coil at a particular location, assigning the location of said predicted stimulation as a seed for a tractography algorithm, determining white matter tracts from the tractography algorithm utilizing the predicted seed, and displaying the predicted white matter tracts on and/or within the combined view. According to certain embodiments the predicted white matter tracts are calculated in real time and displayed prior to stimulation of the location.

Depending on the processing power of the system implementing the present method(s) and/or the complexity of the tractography algorithm, the calculation of predicted white matter tracts may be substantially real-time or may include a delay of some length. If a delay in the calculation is predicted or expected then it can be desirable for the operator to manually tag the location at which they would like the system to predict the white matter tracts. This can be done by a known input mechanism, for instance when the coil is in a desired position. The position and orientation of the coil can also be logged. Once the calculations are complete and the predicted white matter tracts are displayed to the operator, if the operator decides that the tracts are acceptable they can re-align the TMS coil and the system may notify or automatically stimulate the subject when the coil is in the proper position, and optionally orientation.

Similarly, the predicted white matter tracts may indicate predicted terminal ends and may allow the operator to stimulate the predicted terminal ends, in place of or in addition to the seed area, by notifying or automatically stimulating the subject when the coil is in the proper position, and optionally orientation. By stimulating the terminal end(s) and measuring or recording the response, it may be possible to determine the accuracy or validity/non-validity of the seed with or without actually stimulating the seed location.

A system according to certain embodiments of the present invention comprises a stereotactic device that can be used to guide a stimulating device with respect to the brain anatomy. A navigation device can be used to guide the stimulating device to an appropriate anatomical location where the stimulating device is activated and induces an E-Field on or in a portion of the brain.

A stereotactic neuronavigation device can guide a TMS coil, or another stimulating device such as cortical stimulation electrodes, tDCS electrodes or DBS leads. Additionally, there can be an image processing module that processes diffusion MRI data leading to maps of anatomical connectivity.

Figure 5:
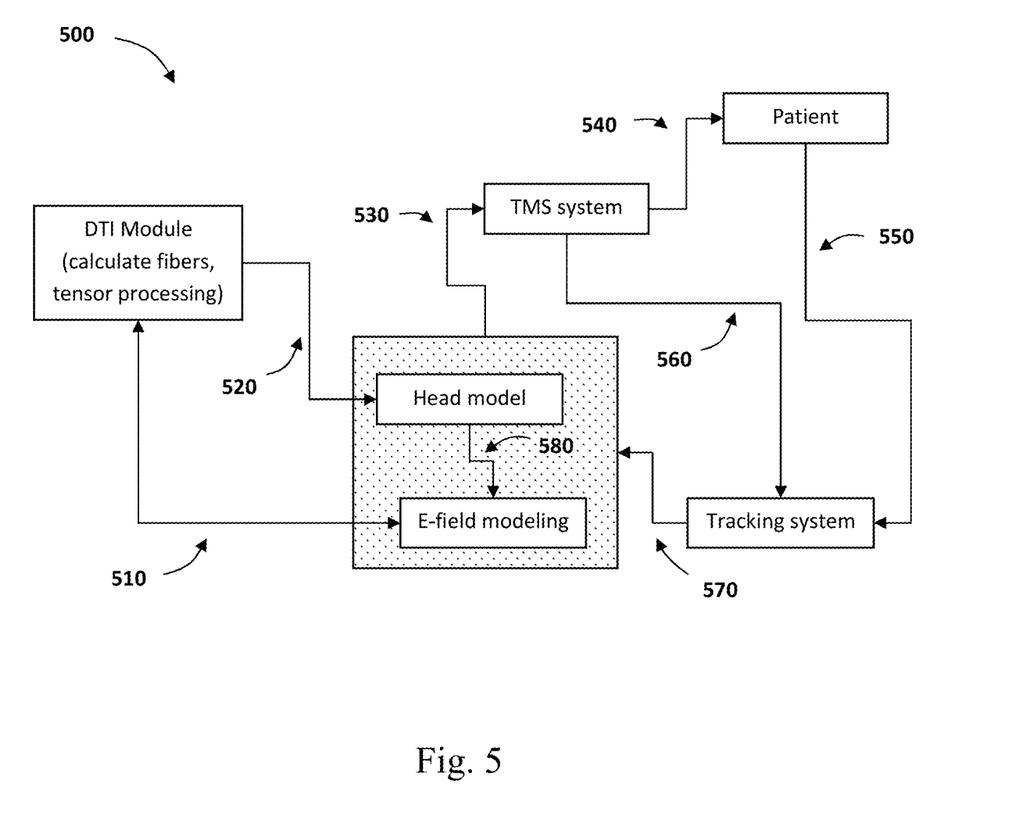
FIG. 5 shows examples of components of a system for combining DTI and NBS (or other stimulation) data.
Figure 6:
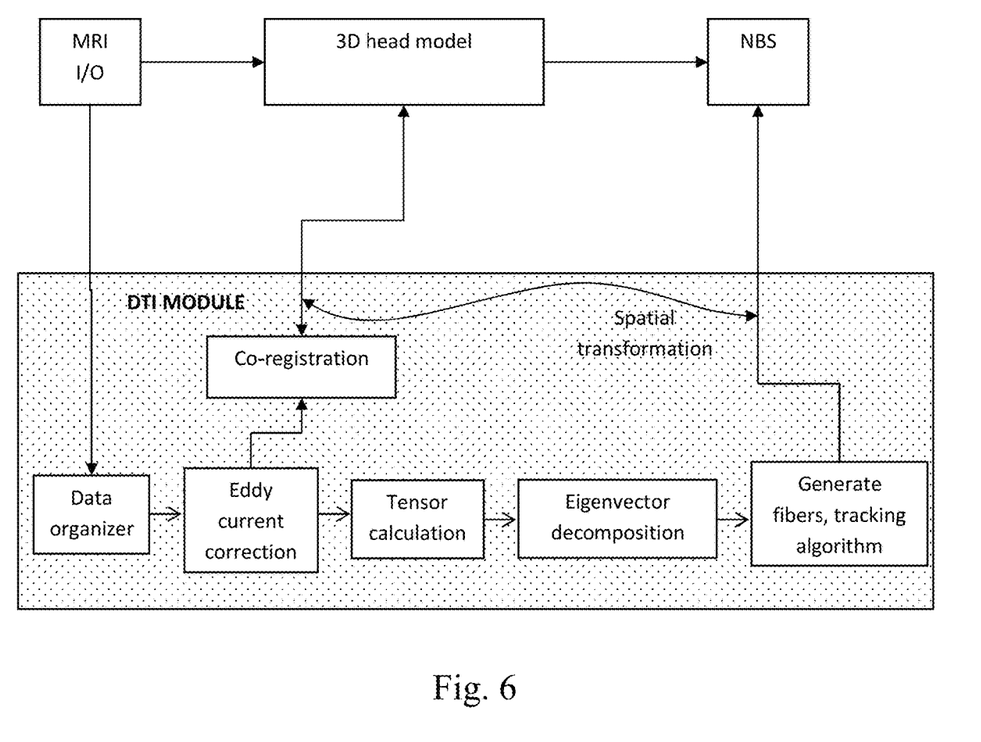
FIG. 6 shows additional examples of components for a system for combining DTI and NBS data.

Examples of systems according to the present invention include a combination of the following elements; (i) a stereotactic navigation device (which can be optical, magnetic, etc.), (ii) a stimulating device aiming to create acute or long term effects in the stimulated area (TMS, transcranial electrical, epidural electrical, optical, ultrasound—based), (iii) a radiotherapy system, said radiotherapy system optionally including a dose calculation system, (iv) a real time physics modeling system (e.g. E-field calculator) for modeling the properties of a stimulating device, (v) an image IO-system reading the image data, (vi) an image processing system for correlating anatomical data to DTI data (e.g. coregistration, overlaying different data sets), (vii) a DTI processing system, said processing system optionally capable of processing other diffusion MR based data, e.g. DSI, Q-Ball data, Q-space data, or other connectivity data obtained from e.g. resting state-fMRI, spontaneous/stimulated EEG or spontaneous/stimulated MEG or functional NIRS, (viii) a system correlating anatomical connectivity (DTI) or functional connectivity information (rs-FMRI) and stereotactic information, for example as shown in FIG. 6, (ix) a system correlating anatomical connectivity (DTI), or functional connectivity information, such as rs-FMRI, MEG or EEG and stereotactic information associated with a real-time physics modeling system. An example of the system components is shown in FIG. 5. Such systems are capable of carrying out the methods described above.

FIG. 5 shows an example of a system 500 for carrying out a method according to the description above. The system 500 has a DTI module which communicates, preferably two ways, with the e-field modeling component of an NBS module. The two-way communication 530 includes seeds from the e-field modeling being sent to the DTI module for calculating fibers and tensor processing. The DTI module is capable of sending information and requests to the e-field modeling module in order to, for example, validate fibers.

Once the DTI module has calculated, and optionally verified, one or more fibers then it can transmit the findings to the head model of the NBS module for display, 520, wherein the head model is in communication with the e-field modeling module, 580. The TMS system communicates with the NBS module to control stimulation, 530. Markers, for instance, on the TMS coil and patient indicate the position of the coil and head to the tracking system, 560 and 550 respectively. The tracking system, which tracks the coil and head positions communicates the position data with the NBS module, 570.

The systems and methods described above have a plurality of uses. One of the exemplary uses is in helping determine seeds for tractography algorithms. The particular seed selection may be based on or including some of the following:

Seeding from different depths, as NBS can stimulate the brain at different depths. Additionally, the selection of best number of tracts to ensure that the seed is on white matter.

Seed selection based on an excitability threshold, for example, a seed is selected from an area exceeding 60 V/m, when the subject's motor threshold at 20 mm depth is 55 V/m.

Seed selection based on normalized motor response. Seeding can be initiated when relation of normalized EMG (mV)/(V/m) exceeds a predefined value.

Seed selection based on normalized brain response. Seeding can be initiated when normalized EEG response (pV)/(V/m) exceeds a predefined value.

Seed selection based on image data properties. For example, when white matter signal intensity (T1 or FA) and E-Field threshold value overlap.

Seed selection based on exclusion or inclusion, e.g. any Boolean operation, between DTI targets and NBS responses. For example, subcortical seeds can be defined and/or chosen and the fibers in connection to responding stimulated areas are mapped.

Seed selection based on response and non response, simultaneous display of fibers originating from a responding and non-responding area.

The present systems and methods can also be used particularly for motor mapping and corticospinal tract identification. For example, they can be used for segmentation of subcortical white matter based on combined information from DTI and navigated brain stimulation device. They may also be used for validation of NBS responses based on existing tracts, based on the proximity of tracks.

Further uses include the selection of stimulation area(s), or grid squares, based on overlapping information from NBS response and DTI. Cross-validation of DTI and NBS, e.g. Boolean operations between fibers and NBS responses, and selection of a number of seeds/tracts based on cortical excitability are attainable via embodiments of the present systems and methods.

Seeding can also be based from center of gravity or an accumulated response map, the result of which may enhance the reliability of resulting fiber tracts. Still yet, targeting of DTI based on NBS responses, e.g. seed placed at posterior limb of internal capsule (PLIC), endpoints or targets are cortical targets obtained with the stimulating device, can be achieved.

More specifically, the present methods and systems can be used in the treatment of depression, visual cortex mapping, speech mapping and stroke therapy to name a few. When treating depression for example, the present methods and system can be used to identify seed placed in limbic structures, e.g. cingulum, or areas associated with functional neuroimaging results, e.g. anterior cingulate gyrus. Additionally, seed placement can be identified in structures associated with identification of BA46/BA9, such as superior longitudinal fasciculus II (SLFII). Still yet, seed placement can be identified within structures associated with the regions associated with the symptoms, speech, sensory etc.

For use in visual cortex mapping the present methods and systems can be used to identify seed placement at the optical tract or optical chiasm, for example. For use in speech mapping, the present methods and systems can be used to identify the tracts from the Broca to the Wernicke, e.g. arcuate fasciculus, prior to or during mapping.

When used in stroke therapy, for example, the present methods and systems can be utilized for identifying Contralateral motor stimulation areas found and targeted for reducing inhibition from the intact hemisphere. Additionally, for dealing with Aphasia, Contralateral speech processing areas, e.g. Broca, Wernicke, cricothyroid cortical representation, can be identified for targeting for reducing cross-hemispheric inhibition from the intact hemisphere.

Furthermore, a computer readable medium or mediums may have stored there on a set or sets of computer readable instructions for causing one or more processors to carry out the steps of any of the methods described above. Said computer readable medium may be transitory or non-transitory in nature.

Although embodiments and examples of the invention have been described in language specific to features and/or methods, one of ordinary skill in the art will recognize countless variations and modifications of features from embodiments, combinations of described embodiments and examples which would not depart from the scope of the present invention. Rather, the specific features and methods are disclosed as example implementations of the present invention.

The invention claimed is:

1. A method for enabling transcranial magnetic stimulation (TMS) treatment, said method comprising the steps of:
   acquiring an anatomical image of a brain of a subject,
   acquiring functional data of the brain of the subject,
   coregistering at least a portion of the functional data, said portion being associated with a portion of interest of the brain, with a corresponding location from the anatomical image in order to form a combined view of the brain, and stereotactically aligning the combined view of the brain and a transcranial magnetic stimulation (TMS) stimulation device in real-time, selecting a location of the brain to stimulate with a TMS pulse from the TMS stimulation device based on the combined view, wherein the location of the brain is selected by:

(a) stimulating the brain of the subject with the TMS stimulation device to generate a predetermined response in the subject, (b) selecting one or more seed locations in the brain that generate the predetermined response, (c) determining white matter tracts that extend from the one or more seed locations to a deep and/or distant target utilizing a tractography algorithm, and (d) after step (c), further stimulating the brain of the subject with the TMS stimulation device at the one or more seed locations to stimulate the deep and/or distant target, wherein, if the step (d) of further stimulating generates a desired response at the deep and/or distant target, treating the brain of the subject with additional stimulation at the one or more seed locations, and wherein, if the step (d) of further stimulating does not generate the desired response at the deep and/or distant target, varying at least one of a stimulation parameter, the tractography algorithm, a tractography algorithm parameter, and the one or more seed locations.

2. The method according to claim 1, further comprising the step of displaying the combined view of the brain having functional data for at least the portion of interest of the brain associated with the corresponding location on the anatomical image.

3. The method according to claim 1, wherein the anatomical image of the brain is stereotactically aligned with a subject's head with TMS navigation software.

4. The method according to claim 1, wherein the location of the brain to stimulate is selected in order to treat depression.

5. The method according to claim 1, wherein the functional data is positron emission tomography (PET) data, functional magnetic resonance imaging (fMRI) data, resting state-fMRI (rsfMRI) or diffusion tensor imaging (DTI) data.

6. The method of claim 1, wherein the tractography algorithm uses the functional data of the brain.

7. The method of claim 6, wherein the functional data of the brain is at least one of: DTI, fMRI and rsfMRI data.

8. The method according to claim 1, further comprising the step of displaying the white matter tracts on or within the combined view.

9. The method according to claim 1, wherein the tractography algorithm is applied in real-time and the results are displayed to a navigated TMS operator during stimulation.

10. The method according to claim 1, further comprising verifying an intracranial connection between the deep and/or distant target and the location of the brain to stimulate by navigated TMS mapping of the location of the brain to stimulate.

11. The method according to claim 1, wherein the location of the brain to stimulate is further selected based on an excitability threshold.

12. The method according to claim 11, wherein the selection of the location of the brain to stimulate is based on an area which when stimulated produces a normalized EMG response exceeding a predefined value.

13. The method according to claim 11, wherein the selection of the location of the brain to stimulate is based on an area which when stimulated produces a normalized EEG response exceeding a predefined value.

14. The method according to claim 1, further comprising the steps of;

tracking a navigated TMS coil in relation to a subject's head, wherein the location and orientation of the subject's head is co-registered with at least a portion of the combined view, assigning the location of the location of the brain to stimulate as the one or more seed locations for the tractography algorithm, determining the white matter tracts from the tractography algorithm utilizing the one or more seed location, and displaying the determined white matter tracts on and/or within the combined view.

15. The method according to claim 4, further comprising the step of:

providing a view of the combined view of the brain containing an indication on the brain network potentially affected by stimulation based on the stereotactically aligned combined view of the brain and the stimulation device and an indication of the location of the brain to stimulate.

16. A non-transitory computer readable medium having stored there on a set of computer readable instructions for causing one or more processors to carry out the steps of claim 1.

17. The method according to claim 1, wherein the location of the brain to stimulate is within structures associated with identification of BA46.

18. The method according to claim 1, wherein the location of the brain to stimulate is within structures associated with identification of BA9.

19. The method according to claim 1, further comprising verifying that the one or more seed locations are desired seed location(s) by stimulating one or more terminal ends of the white matter tracts determined by the tractography algorithm, and determining whether the stimulating of the one or more terminal ends also triggers the predetermined response in the subject.

* * * * *